(12) United States Patent
Pinsonneault (10) Patent No.: US 8,036,914 B1
(45) Date of Patent: Oct. 11, 2011

(54) SYSTEMS AND METHODS FOR SUPPORTING DRUG OR PRODUCT RECALLS

(75) Inventor: Roger Pinsonneault, Alpharetta, GA (US)

(73) Assignee: McKesson Financial Holdings Limited, Hamilton (BM)

( * ) Notice: Subject to any disclaimer, the term of this patent is extended or adjusted under 35 U.S.C. 154(b) by 290 days.

(21) Appl. No.: 12/388,956

(22) Filed: Feb. 19, 2009

(51) Int. Cl.
*G06Q 50/00* (2006.01)
(52) U.S. Cl. .......................................... 705/2
(58) Field of Classification Search .................. 705/2, 3
See application file for complete search history.

(56) References Cited

U.S. PATENT DOCUMENTS

| | | | |
|---|---|---|---|
| 5,628,530 A | 5/1997 | Thornton | |
| 6,012,035 A | 1/2000 | Freeman et al. | |
| 6,757,898 B1 | 6/2004 | Ilsen et al. | |
| 6,769,228 B1 | 8/2004 | Mahar | |
| 7,155,397 B2 | 12/2006 | Alexander et al. | |
| 2001/0029483 A1* | 10/2001 | Schultz et al. | 705/39 |
| 2001/0056359 A1* | 12/2001 | Abreu | 705/3 |
| 2002/0002495 A1 | 1/2002 | Ullman | |
| 2002/0032582 A1* | 3/2002 | Feeney et al. | 705/2 |
| 2002/0087583 A1 | 7/2002 | Morgan et al. | |
| 2002/0111832 A1 | 8/2002 | Judge | |
| 2002/0198831 A1 | 12/2002 | Patricelli et al. | |
| 2003/0009367 A1 | 1/2003 | Morrison | |
| 2003/0050799 A1 | 3/2003 | Jay et al. | |
| 2003/0149625 A1 | 8/2003 | Leonardi et al. | |
| 2003/0154163 A1 | 8/2003 | Phillips et al. | |
| 2003/0229540 A1 | 12/2003 | Algiene | |
| 2004/0039599 A1 | 2/2004 | Fralic | |
| 2004/0073457 A1 | 4/2004 | Kalies | |
| 2004/0078234 A1 | 4/2004 | Tallal, Jr. | |
| 2004/0117323 A1 | 6/2004 | Mindala | |
| 2004/0148198 A1 | 7/2004 | Kalies | |

(Continued)

FOREIGN PATENT DOCUMENTS

CA 2482370 3/2006
(Continued)

OTHER PUBLICATIONS

Sampson, R.J., Taking Control of Health Care Costs, Best's Review—Life Health Insurance Edition, Nov. 1983, pp. 64-66, vol. 84, Issue 7, USA.

(Continued)

*Primary Examiner* — Gerald J. O'Connor
*Assistant Examiner* — Trang Nguyen
(74) *Attorney, Agent, or Firm* — Sutherland Asbill & Brennan LLP (57) ABSTRACT

Systems and methods may be provided for supporting drug or product recalls. The systems and methods may include receiving a healthcare transaction request from a pharmacy computer associated with a pharmacy, wherein the healthcare transaction request includes an identification of a prescribed drug or product; determining, based upon the identification of the prescribed drug or product, that the prescribed drug or product is associated with a recall; providing, in response to the determination that the prescribed drug or product is associated with the recall, a response that includes information for accessing a web portal interface; receiving, over the web portal interface, lot numbers associated with pharmacy inventory of the prescribed drug or product; determining that one or more of the received lot numbers are affected by the recall; and generating a notification identifying the received lot numbers that are associated with the pharmacy inventory.

20 Claims, 7 Drawing Sheets

U.S. PATENT DOCUMENTS

| | | |
|---|---|---|
| 2004/0249745 A1 | 12/2004 | Baaren |
| 2005/0015280 A1 | 1/2005 | Gabel et al. |
| 2005/0060201 A1 | 3/2005 | Connely et al. |
| 2005/0102169 A1 | 5/2005 | Wilson |
| 2005/0154627 A1 | 7/2005 | Zuzek et al. |
| 2005/0187793 A1 | 8/2005 | Myles |
| 2005/0197862 A1 | 9/2005 | Paterson et al. |
| 2005/0240473 A1 | 10/2005 | Ayers |
| 2005/0288972 A1 | 12/2005 | Marvin et al. |
| 2006/0020514 A1 | 1/2006 | Yered |
| 2006/0026041 A1 | 2/2006 | Ullman et al. |
| 2006/0149784 A1 | 7/2006 | Tholl et al. |
| 2006/0184391 A1 | 8/2006 | Barre et al. |
| 2006/0224417 A1* | 10/2006 | Werner ............ 705/2 |
| 2006/0259363 A1 | 11/2006 | Jhetam |
| 2007/0005402 A1 | 1/2007 | Kennedy et al. |
| 2007/0050209 A1 | 3/2007 | Yered |
| 2007/0136100 A1 | 6/2007 | Daugherty et al. |
| 2007/0233525 A1 | 10/2007 | Boyle |
| 2007/0233526 A1 | 10/2007 | Hoffman et al. |
| 2007/0239493 A1 | 10/2007 | Sweetland et al. |
| 2008/0262948 A1* | 10/2008 | Grady et al. .......... 705/28 |
| 2010/0030667 A1* | 2/2010 | Chudy et al. .......... 705/28 |

FOREIGN PATENT DOCUMENTS

| | | |
|---|---|---|
| WO | 9503569 | 2/1995 |
| WO | 0039737 | 7/2000 |
| WO | 2007025295 | 3/2007 |

OTHER PUBLICATIONS

Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

Lamb, J., New Era of Electronic Medicine Management: E-Prescriptions, Britain's Traditionally Cautious National Health Service is Starting Trials for Online Prescription, with the Aim of Cutting Costs. Financial Times, London, Feb. 21, 2001, p. 6, London, United Kingdom.

Anonymous, Pharmacy Industry Leaders Launch Firm to Supply Real-Time Data. PR Newswire. Jul. 30, 2001, p. 1, New York, NY, USA.

Anonymous, Medic: On-line Goes In-House, Chain Store Age Executive, Jan. 1987, pp. 128-132. vol. 63, Issue 1, USA.

Anonymous, TechRx Announces Successful Beta Deployment of T-Rex. PR Newswire. May 13, 2002.

* cited by examiner

Drug Recall Network

Notice of [Drug or Product Name] Recall

[Manufacturer] has issued a recall for [Drug Name]. To determine whether any recalled lots are in your inventory, please visit www.[service_provider].com/productrecalls and enter Transaction ID [ABCDEFG]. Questions? Call (800) XXX-XXXX

< EXIT >

SYSTEMS AND METHODS FOR SUPPORTING DRUG OR PRODUCT RECALLS

FIELD OF THE INVENTION

Aspects of the invention relate generally to drug or product recalls, and more particularly, to systems and methods for supporting drug or product recalls.

BACKGROUND OF THE INVENTION

Once a drug or product is in widespread use, unforeseen problems can sometimes lead to a recall. When a prescription drug or product is either defective or potentially harmful, recalling that product—removing it from the market or correcting the problem—is the most effective means for protecting the public. Accordingly, there is a need in the industry for systems and methods for supporting drug or product recalls.

SUMMARY OF THE INVENTION

According to an example embodiment of the invention, there is a method for supporting drug or product recalls. The method may include receiving, by a service provider, a healthcare transaction request from a pharmacy computer associated with a pharmacy, where the healthcare transaction request includes an identification of a prescribed drug or product; determining, by the service provider based upon the identification of the prescribed drug or product, that the prescribed drug or product is associated with a recall; providing, by the service provider in response to the determination that the prescribed drug or product is associated with the recall, a response that includes information for accessing a web portal interface; receiving, by the service provider over the web portal interface, lot numbers associated with pharmacy inventory of the prescribed drug or product; determining, by the service provider, that one or more of the received lot numbers are affected by the recall; and generating, by the service provider, a notification identifying the received lot numbers that are associated with the pharmacy inventory.

According to another example embodiment of the invention, there is a system for supporting drug or product recalls. The system may include a memory for storing computer-executable instructions, and a processor configured to access the memory. The processor may be further configured to execute the computer-executable instructions to receive a healthcare transaction request from a pharmacy computer associated with a pharmacy, where the healthcare transaction request includes an identification of a prescribed drug or product; determine, based upon the identification of the prescribed drug or product, that the prescribed drug or product is associated with a recall; provide, in response to the determination that the prescribed drug or product is associated with the recall, a response that includes information for accessing a web portal interface; receive, over the web portal interface, lot numbers associated with pharmacy inventory of the prescribed drug or product; determine that one or more of the received lot numbers are affected by the recall; and generate a notification identifying the received lot numbers that are associated with the pharmacy inventory.

BRIEF DESCRIPTION OF THE DRAWINGS

Reference will now be made to the accompanying drawings, which are not necessarily drawn to scale, and wherein.

DETAILED DESCRIPTION

Embodiments of the invention will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those of ordinary skill in the art. Like numbers refer to like elements throughout.

Embodiments of the invention may be directed towards systems and methods for supporting drug or product recalls. According to an example embodiment, the systems and methods may provide a service provider that monitors a healthcare transaction request from a pharmacy computer to determine whether a healthcare transaction request specifies a drug or product that may be potentially recalled. If the service provider determines that the drug or product may be potentially recalled, then the service provider may provide a response or message to a pharmacy computer that directs the pharmacy to access a web portal interface. At the web portal interface, the pharmacy employee may provide lot numbers (or another similar identifier) for the pharmacy inventory of the drug or product that may be potentially affected by the drug or product recall. If the service provider verifies that any of the pharmacy inventory—that is, particular lot numbers—are actually affected by or subject to the recall, then the service provider may notify the pharmacy (and recall logistics entity) of the particular lots that are being recalled, and may also direct a recall logistics entity to recover, obtain, or otherwise destroy the recalled inventory. The pharmacy may obtain reimbursement for the recalled inventory by submitting a pharmacy claim request to the service provider.

System Overview

Figure 1:
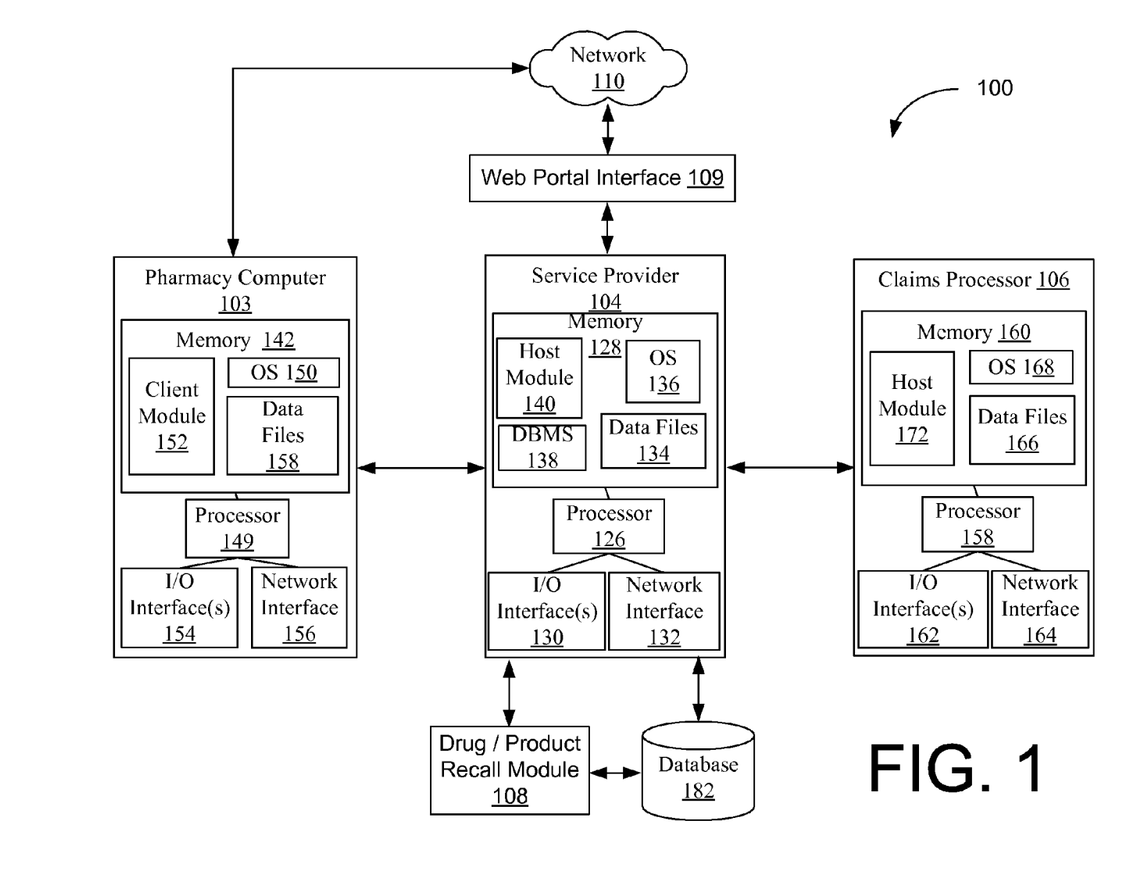
FIG. 1 illustrates an example system for supporting drug or product recalls, according to an example embodiment of the invention.

FIG. 1 illustrates an example system 100 for supporting drug or product recalls, according to an example embodiment of the invention. As shown in FIG. 1, the system 100 may include a pharmacy computer 103, a service provider 104, and a claims processor 106, which are each configured for accessing and reading associated computer-readable media having stored thereon data and/or computer-executable instructions for implementing the various methods of the invention. Generally, network devices and systems, including the one or more pharmacy computers 103, service providers 104, and claims processors 106 have hardware and/or software for transmitting and receiving data and/or computer-executable instructions over a communications link and a memory for storing data and/or computer-executable instructions. These network devices and systems may also include a processor for processing data and executing computer-executable instructions, as well as other internal and peripheral components that are well known in the art. As used herein, the term "computer-readable medium" may describe any form of memory or a propagated signal transmission medium. Propagated signals representing data and computer program instructions may be transferred between network devices and systems.

As shown in FIG. 1, the pharmacy computer 103, service provider 104, and claims processor 106 may be in communication with each other via a network such as network 110, which as described below can include one or more separate or shared private and public networks, including the Internet or a publicly switched telephone network. Each of these components—the pharmacy computer 103, the service provider 104, the claims processor 106, and the network 110—will now be discussed in further detail.

First, the pharmacy computer 103 may be any processor-driven device, such as a personal computer, laptop computer, handheld computer, and the like. In addition to having a processor 149, the pharmacy computer 103 may further include a memory 142, input/output ("I/O") interface(s) 154, and a network interface 156. The memory 142 may store data files 158 and various program modules, such as an operating system ("OS") 150 and a client module 152. The memory 142 may be any computer-readable medium, coupled to the processor 149, such as RAM, ROM, and/or a removable storage device for storing data files 158 and a database management system ("DBMS") to facilitate management of data files 158 and other data stored in the memory 142 and/or stored in separate databases. The OS 150 may be, but is not limited to, Microsoft Windows®, Apple OSX™, Unix, or a mainframe operating system. The client module 152 may be an Internet browser or other software, including a dedicated program, for interacting with the service provider 104 and/or the claims processor 106. For example, a user such as a pharmacist or other pharmacy employee may utilize the client module 152 in preparing and providing a prescription claim request to the service provider 104 for delivery to the appropriate claims processor 106. The pharmacy computer 103 may also utilize the client module 152 to retrieve or otherwise receive data, messages, or responses from the service provider 104.

Still referring to the pharmacy computer 103, the I/O interface(s) 154 may facilitate communication between the processor 149 and various I/O devices, such as a keyboard, mouse, printer, microphone, speaker, monitor, bar code readers/scanners, RFID readers, and the like. The network interface 156 may take any of a number of forms, such as a network interface card, a modem, a wireless network card, and the like. It will be appreciated that while pharmacy computer 103 has been illustrated as a single computer or processor, the pharmacy computer 103 may be comprised of a group of computers or processors, according to an example embodiment of the invention.

The service provider 104 may include, but is not limited to, any processor-driven device that is configured for receiving, processing, and fulfilling requests from the pharmacy computer 103 and/or claims processor 106 relating to prescription, pharmacy, benefits, and/or claim transactions or other activities. According to an example embodiment of the invention, the service provider 104 may comprise, but is not limited to, one or more "switches" or "switch providers" performing routing and processing of prescription transactions between or among pharmacies, payors/claims processors, and/or other service providers.

The service provider 104 may include a processor 126, a memory 128, input/output ("I/O") interface(s) 130, and a network interface 132. The memory 128 may be any computer-readable medium, coupled to the processor 126, such as RAM, ROM, and/or a removable storage device for storing data files 134 and a database management system ("DBMS") 138 to facilitate management of data files 134 and other data stored in the memory 128 and/or stored in one or more databases 144. The memory 128 may store data files 134 and various program modules, such as an operating system ("OS") 136, a database management system ("DBMS") 138, and the host module 140. The OS 136 may be, but is not limited to, Microsoft Windows®, Apple OSX™, Unix, or a mainframe operating system.

The data files 134 may also store routing tables for determining the destination of communications received from the pharmacy computer 103 or claims processor 106. The host module 140 may receive, process, and respond to requests from the client module 152 of the pharmacy computer 103, and may further receive, process, and respond to requests from the host module 172 of the claims processor 106. The database 182 may be one or more databases operable for storing information that supports a drug or product recall process, according to an example embodiment of the invention. As an example, the database 182 may store information that indicates one or more lot numbers for one or more respective drugs or products that are subject to a recall.

A drug/product recall module 108 may also be operative with the service provider 104. The drug/product recall module 108 may include computer-executable instructions for supporting a drug or product recall process, as described herein. As an example, the drug/product recall module 108 may be operative to determine whether one or more lot numbers for a particular drug or product are affected by a recall. In addition, the drug/product recall module 108 may also be able to direct recovery of inventory corresponding to the affected lot numbers for a particular drug or product. These and other operations of the drug/product recall module 108 are discussed herein. The drug/product recall module 108 may be implemented as computer-implemented instructions of the memory 128 of the service provider 104. Alternatively, the drug/product recall module 108 may also be implemented as computer-implemented instructions of a memory of separate processor-based system, according to an example embodiment of the invention.

In addition, a web portal interface 109 may also be operative with or otherwise associated with the service provider 104. In particular, the web portal interface 109 may allow for a pharmacy computer 103 or another computer to access the service provider 104 from outside of a healthcare transaction processing network. For example, a pharmacy computer 103 may access the web portal interface 109 via a network such as network 110, which may include the Internet. According to an example embodiment of the invention, the pharmacy computer 103 or another computer may access the web portal interface 109 via a network such as network 110 to otherwise determine whether pharmacy inventory of a drug or product may be subject to or otherwise affected by a recall.

The web portal interface 109 may be provided by a separate processor-based system that is distinct from the service provider 104. By way of example, the web portal interface 109 may be provided by a web server that is in communication with network 110 and the service provider 104. Alternatively, it will be appreciated that the web portal interface 109 may also be incorporated into the service provider 104 as well, according to another example embodiment of the invention. The web portal interface 109 may be associated with one or more universal resource locators (URLs) or website addresses, according to an example embodiment of the invention.

The claims processor 106 may be any processor-driven device, such as, but not limited to, a server computer, a mainframe computer, one or more networked computers, a desktop computer, a personal computer, a laptop computer, a mobile computer, a handheld portable computer, a digital assistant, a personal digital assistant, a digital tablet, an Internet appliance, or any other processor-based device. The claims processor 106 may include a processor 158, a memory 160, input/output ("I/O") interface(s) 162, and a network interface 164. The memory 160 may be any computer-readable medium, coupled to the processor 158, such as RAM, ROM, and/or a removable storage device for storing data files 166 and a database management system ("DBMS") to facilitate management of data files 166 and other data stored in the memory 160 and/or stored in separate databases. The memory 160 may store data files 166 and various program modules, such as an operating system ("OS") 168, a database management system ("DBMS"), and a host module 172. The OS 168 may be, but is not limited to, Microsoft Windows®, Apple OSX™, Unix, or a mainframe operating system. The host module 172 may receive, process, and respond to requests from the client module 122 of pharmacy computer 103, and may further receive, process, and respond to requests from the host module 140 of the service provider 104. According to an example embodiment of the invention, the claims processor 106 may be associated with benefits determination by a discount program, an insurance company, a pharmacy benefits manger (PBM), a government payor, or another third-party payor. According to an alternative example embodiment of the invention, a claims processor 106 may also be implemented as part of a service provider 104.

Still referring to the claims processor 106, the I/O interface(s) 162 may facilitate communication between the processor 158 and various I/O devices, such as a keyboard, mouse, printer, microphone, speaker, monitor, bar code readers/scanners, RFID readers, and the like. The network interface 164 may take any of a number of forms, such as a network interface card, a modem, a wireless network card, and the like. It will be appreciated that while the claims processor 106 has been illustrated as a single computer or processor, the claims processor 106 may be comprised of a group of computers or processors, according to an example embodiment of the invention.

The network 110 may include any telecommunication and/or data network, whether public, private, or a combination thereof, including a local area network, a wide area network, an intranet, an internet, the Internet, intermediate hand-held data transfer devices, a publicly switched telephone network (PSTN), and/or any combination thereof and may be wired and/or wireless.

Generally, each of the memories and data storage devices, such as the memories 142, 128, 160 and the database 182, and/or any other memory and data storage device, can store data and information for subsequent retrieval. In this manner, the system 100 can store various received or collected information in memory or a database associated with one or more pharmacy computers 103, service providers 104, and/or claims processors 106. The memories and databases can be in communication with each other and/or other databases, such as a centralized database, or other types of data storage devices. When needed, data or information stored in a memory or database may be transmitted to a centralized database capable of receiving data, information, or data records from more than one database or other data storage devices. In other embodiments, the databases shown can be integrated or distributed into any number of databases or other data storage devices. In one example embodiment, for security, the service provider 104 (or any other entity) may have a dedicated connection to the database 182, as shown; though, in other embodiments, the service provider 104 or another entity may communicate with the database 142 via a network such as network 110.

Suitable processors, such as the processors 149, 126, 158 of the pharmacy computers 103, service providers 104, and/or claims processors 106, respectively, may comprise a microprocessor, an ASIC, and/or a state machine. Example processors can be those provided by Intel Corporation (Santa Clara, Calif.), AMD Corporation (Sunnyvale, Calif.), and Motorola Corporation (Schaumburg, Ill.). Such processors comprise, or may be in communication with media, for example computer-readable media, which stores instructions that, when executed by the processor, cause the processor to perform the elements described herein. Embodiments of computer-readable media include, but are not limited to, an electronic, optical, magnetic, or other storage or transmission device capable of providing a processor with computer-readable instructions. Other examples of suitable media include, but are not limited to, a floppy disk, CD-ROM, DVD, magnetic disk, memory chip, ROM, RAM, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. The instructions may comprise code from any computer-programming language, including, for example, C, C++, C#, Visual Basic, Java, Python, Perl, and JavaScript. Furthermore, any of the processors may operate any operating system capable of supporting locally executed applications, client-server based applications, and/or browser or browser-enabled applications.

The system 100 shown in and described with respect to FIG. 1 is provided by way of example only. Numerous other operating environments, system architectures, and device configurations are possible. Other system embodiments can include fewer or greater numbers of components and may incorporate some or all of the functionality described with respect to the system components shown in FIG. 1. For example, in one example embodiment, the service provider 104 (or the pharmacy computer 103/claims processor 106) may be implemented as a specialized processing machine that includes hardware and/or software for performing the methods described herein. In addition, the processor and/or processing capabilities of the service provider 104 and/or the drug/product recall module 108, may be implemented as part of the pharmacy computer 103, the claims processor 106, or any combination or portion thereof. Accordingly, embodiments of the invention should not be construed as being limited to any particular operating environment, system architecture, or device configuration.

Operational Overview

Figure 2A:
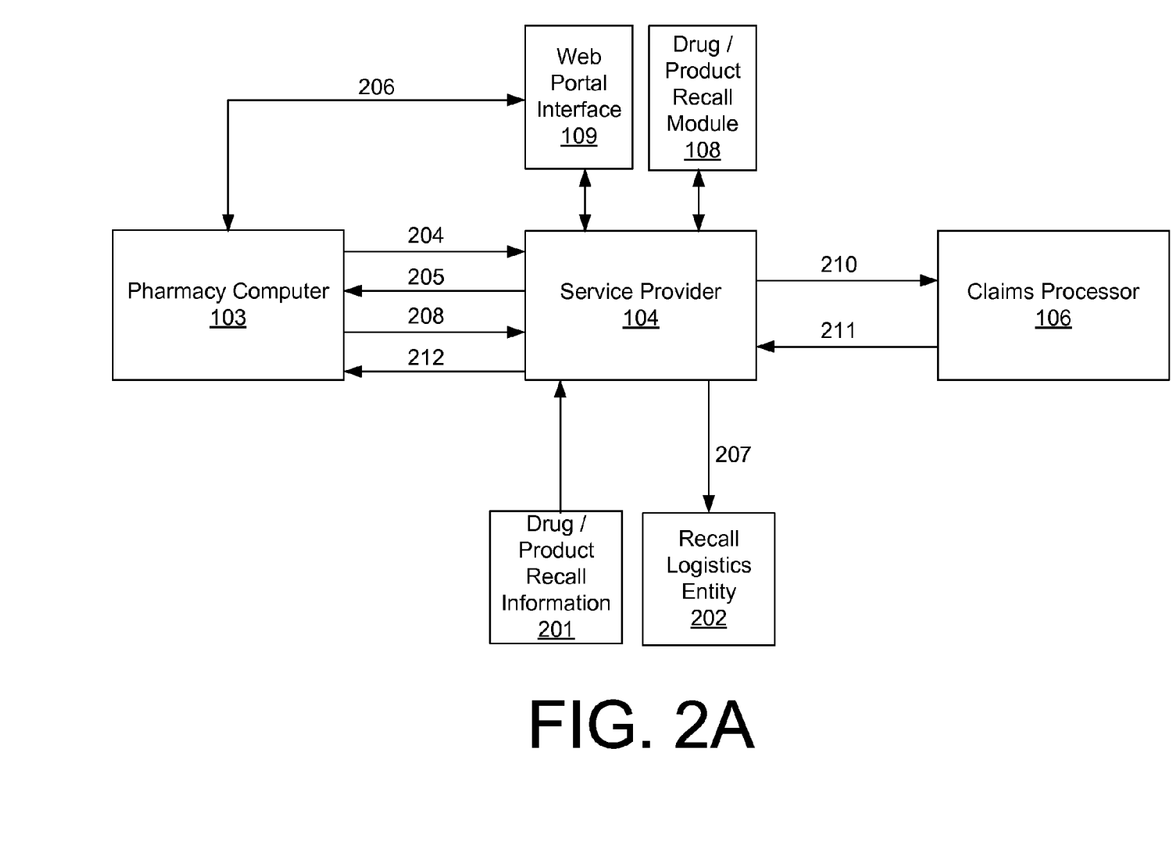
FIG. 2A illustrates a block diagram for an example drug or product recall process, according to an example embodiment of the invention.

FIG. 2A illustrates a block diagram for an example drug or product recall process, according to an example embodiment of the invention. The operation of the block diagram of FIG. 2A will be discussed in conjunction with the flow diagram of FIGS. 3A-3B.

Figure 3A:
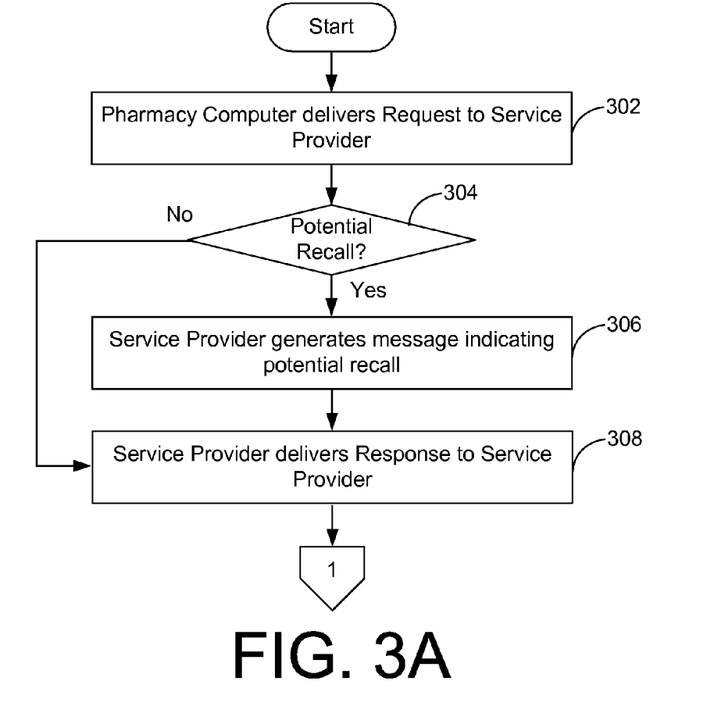
FIGS. 3A-3B illustrates a flow diagram for an example drug or product recall process, according to an example embodiment of the invention.
Figure 3B:
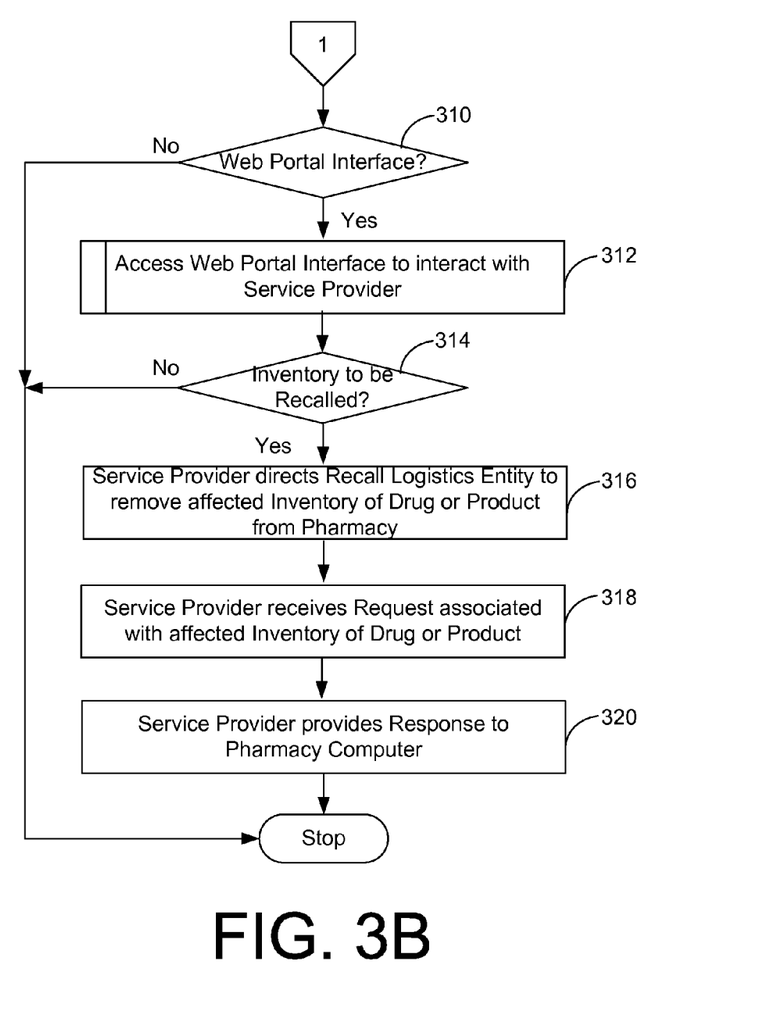

Referring now to FIGS. 2A and 3A-3B, in block 302, a pharmacy computer 103 may transmit, deliver, or otherwise provide a claim request 204 to a service provider 104. The claim request 204 may be in accordance with a version of an NCPDP standard, according to an example embodiment of the invention. For example, the claim request 204 may include one or more of the following information:

Prescriber information
a. Name of the prescriber
b. Prescriber identifier for a physician or healthcare provider Pharmacy information
a. Identifier of the pharmacy submitting the claim request Patient Information
a. Insurance or coverage information
b. Name, address, date of birth
c. Patient Diagnosis/Condition Prescription Information:
a. Identification of the prescribed drug or product (e.g., National Drug Code (NDC))
b. Prescription number
c. Quantity and/or days supply of the prescribed drug or product
d. Pricing information for the prescribed drug or product
e. Date prescription written.

It will be also appreciated that while some example information has been illustrated for the example claim request 204, alternate or additional information may also be included without departing from example embodiments of the invention. For example, the claim request 204 may further include additional patient information such as a gender code for the patient. The claim request 204 may also include a Banking Identification Number (BIN) and Processor Control Number (PCN) for identifying a claims processor 106 as a destination of the request 204.

In block 304, the service provider 104 may deliver a copy of the claim request 204, or at least an identification of the prescribed drug or product in the claim request 204, to the drug/product recall module 108. Where the drug/product recall module 108 is part of the service provider 104, the delivery of a copy of the claim request 204 (or the identification of the prescribed drug or product in the claim request 204) may be an internal delivery. However, where the drug/product recall module 108 is distinct from the service provider 104, then the delivery of the copy of the claim request 204 (or identification of the prescribed drug or product in the claim request 204) may be an external delivery, perhaps via a network such as network 110, according to an example embodiment of the invention.

In block 304, the drug/product recall module 108 may determine whether the prescribed drug or product identified by the claim request 204 is the subject of a potential recall. In making this determination in block 304, the drug/product recall module 108 may access, perhaps via service provider 104, drug/product recall information 201. The drug/product recall module 108 may compare the prescribed drug or product to the drug/product recall information 201 to determine whether the prescribed drug or product is the subject of a potential recall.

The drug/product recall information 201 may be accessed from database 182 or another source, including a network source or an Internet-based source. In an example embodiment of the invention, the drug/product recall information 201 may identify one or more recalled drugs or products, perhaps by National Drug Code (NDC). If a recall is only for certain lot numbers (or other unique identifiers) of drugs or products, then the drug/product recall information can also specify the lot numbers (or other unique identifiers) that are being recalled. It will be appreciated that the drug/product recall information 201 may be provided from a pharmaceutical manufacturer, a distributor, a governmental agency (e.g., FDA), or yet another entity without departing from example embodiments of the invention.

If the drug/product recall module 108 in block 304 determines that the prescribed drug or product identified by the claim request 204 is the subject of a potential recall, then processing may proceed to block 306. In block 306, the service provider 104 may generate a message indicating that the prescribed drug or product is the subject of a potential recall. In addition, the message may also include instructions to the pharmacy to access a web portal interface 109 for determining whether there are any recalled lots of the drug or product in its inventory.

In block 308, the service provider 104 may deliver a response 205 to the request 204 to the pharmacy computer 103. The information included in the response 205 may vary depending on whether a potential recall was identified in block 304:

If no potential recall was identified in block 304, then the service provider 104 may have previously delivered a copy of the claim request 204 to the claims processor 106 as a request 210 for adjudication or other benefits determination by a discount program, pharmacy benefits manager, governmental payor, or another third-party payor. The claims processor 106 may have adjudicated the request 210 and provided a response 211 to the service provider 104. The response 211 may include coverage information, including a covered amount and a patient-responsible amount (e.g., co-pay amount, co-insurance amount, deductible amount, etc.). The service provider 104 may then deliver a copy of the received response 211 to the pharmacy computer 103 as a response 205.

On the other hand, if a potential recall was identified in block 304, then the response 205 in block 308 may include at least the message generated in block 306 to notify the pharmacy of the potential recall and/or availability of the web portal interface 109. In addition, if the transaction was not halted—that is, the request 210 was delivered to the claims processor 106 for adjudication, then the response 205 may also include at least a portion of the information from the response 211 received by the service provider 104 from the claims processor 106.

It will be also be appreciated that the response 205 may also be comprised of two or more distinct responses that may be delivered at different times. For example, there may be a first response delivered at a first time that includes a message notifying the pharmacy of a potential recall and/or availability of the web portal interface 109. Likewise, there may be a second response delivered at a second time that includes information from the response 211 received by the service provider 104 from the claims processor 106. Many variations will be available in accordance with example embodiments of the invention.

Figure 4:
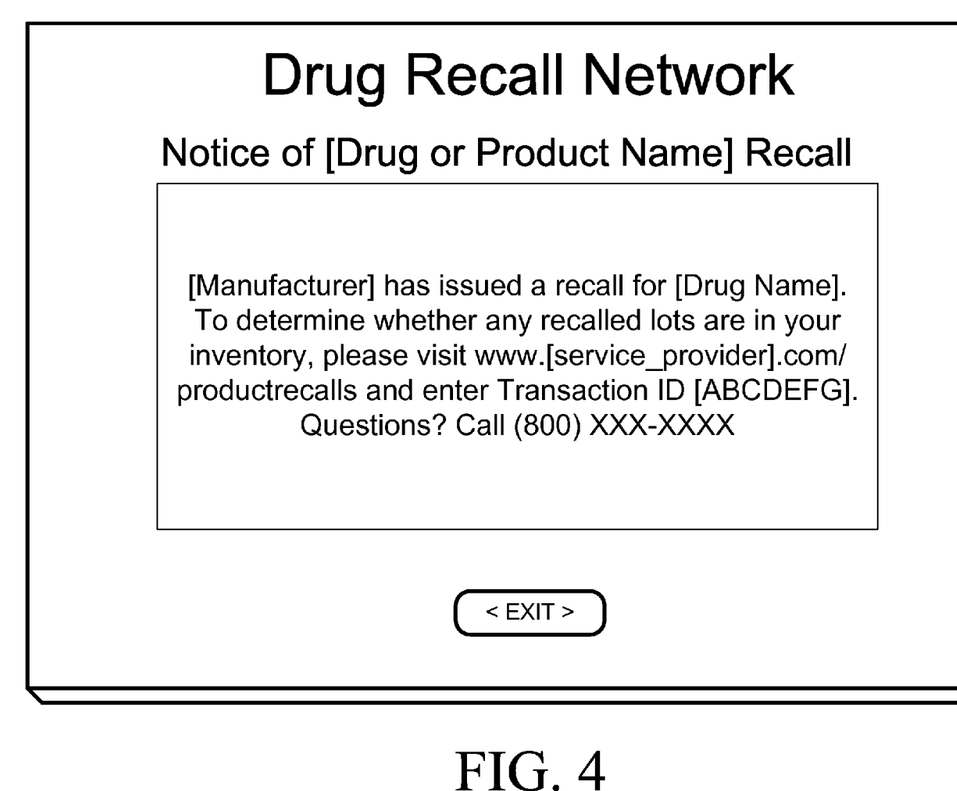
FIG. 4 illustrates an example message that may be delivered from the service provider to the pharmacy computer in accordance with an example drug or product recall process, according to an example embodiment of the invention.

In block 310, the pharmacy computer 103 may receive the response 205 delivered from the service provider 104. The response 205 may include a message notifying the pharmacy that access to a web portal interface 109 is available, as illustrated by FIG. 4. For example, as shown in FIG. 4, the message may include a website address or URL associated with the web portal interface 109. The message may also include an access code or transaction ID (e.g., an alphanumeric code), which may or may not be unique, that the pharmacy computer 103 or another computer may provide when accessing the web portal interface 109. The access code or transaction ID may be utilized in order to identify a particular pharmacy, transaction, or drug/product.

If the response 205 in block 310 includes a message notifying the pharmacy that access to a web portal interface 109 is available, then processing may proceed to block 312. In block 312, a user such as a pharmacist or other pharmacy employee/associate may utilize a computer such as a pharmacy computer 103 to interact with the web portal interface 109 to determine whether the pharmacy includes any pharmacy inventory of a drug or product that is actually affected by the recall. An example process for block 312 will now be discussed in further detail with respect to FIG. 5.

Figure 5:
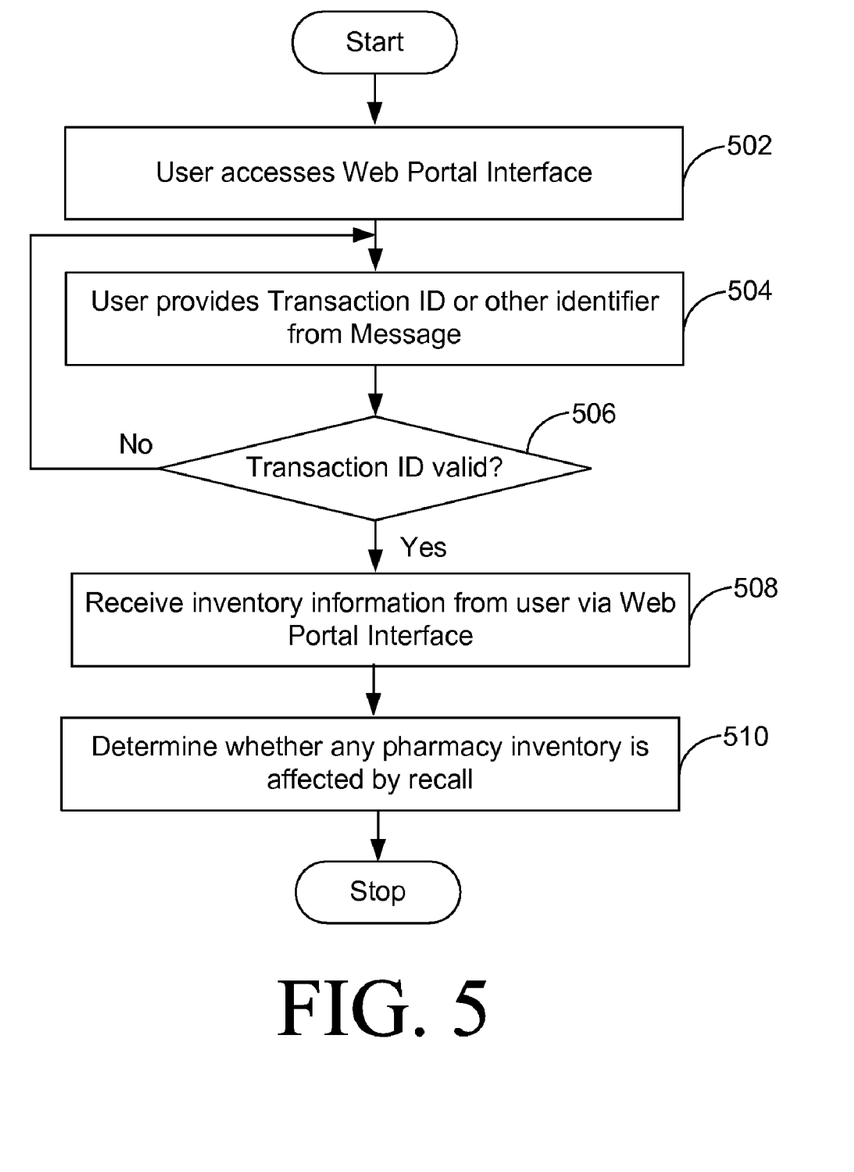
FIG. 5 illustrates an example flow diagram for accessing and interacting with the web portal interface in according with an example drug or product recall process, according to an example embodiment of the invention.

Turning now to block 502 of FIG. 5, a user may utilize a computer such as the pharmacy computer 103 to operate a software program such as an Internet browser to access the web portal interface 109 via the communications link 206 (e.g., via the Internet using network 110). At the web portal interface 109 (e.g., a webpage/website associated with a URL or website location), the pharmacy computer 103 may provide at least the access code or transaction ID received in the response 205, as provided by block 504. It will be appreciated that the access code or transaction ID may also be provided as part of the website address or URL, according to an example embodiment of the invention.

In block 506, the web portal interface 109 may interact with the service provider 104 in validating the received access code or transaction ID. The validation may include determining whether the received access code or transaction ID was previously provided to the pharmacy computer 103 as part of the response 205. The validation may also include determining whether the received access code or transaction ID has expired. It will be appreciated that other validations steps or alternative validation steps may be utilized in block 506, according to an example embodiment of the invention.

Assuming that block 506 results in a determination that the received access code or transaction ID is valid, then the service provider 104 may determine that access code or transaction ID is associated with a potential drug or product recall. Accordingly, the service provider 104 via the web portal interface 109 may request pharmacy inventory information associated with the potentially recalled drug or product. In block 508, the service provider 104 may receive the pharmacy inventory information via the web portal interface 109. According to an example embodiment of the invention, the received pharmacy inventory information may include one or more lot numbers of a drug or product. In block 510, the service provider 104 may determine whether any pharmacy inventory is actually affected by or subject to the recall. For example, the service provider 104 may compare any received lot numbers to drug/product recall information 201 to determine whether the identified lot numbers is actually affected by or subject to the recall. If any of the received lot numbers match the recalled lot numbers specified by the drug/product recall information 201, then there may be pharmacy inventory that is to be recalled.

It will be appreciated that the web portal interface 109 may also request and receive additional information from the pharmacy. As an example, a pharmacist, pharmacy employee, or other user may provide, via the web portal interface 109, information in response one or more questions presented on the web portal interface 109 relating to a particular drug or product that is potentially being recalled. In addition, the pharmacy's interactions with the web portal interface 109 may affect or change one or more messaging options or preferences at the service provider 104. For example, a service provider 104 may determine that the pharmacy has previously responded to a prior notification message relating to a potential drug recall by visiting the web portal interface 109 and providing the access code or transaction ID and/or the lot numbers for a drug or product. In this case, the service provider 104 may suppress, disable, or otherwise not provide future messages from the service provider 104 notifying the pharmacy of a potential recall of a particular drug or product and/or availability of the web portal interface 109. In another example embodiment, the pharmacy may adjust messaging preferences of the service provider 104 by interacting with the web portal interface 109. Many variations are available in accordance with example embodiments of the invention.

Returning to FIG. 3B, in block 314, the service provider 104 may determine that there is pharmacy inventory to be recalled, and processing may proceed to block 316. In block 316, the service provider 104 may generate recall information that identifies the particular lot numbers (or other unique identifier) of the drug or product in the pharmacy's inventory that are being recalled. The recall information may be delivered by the service provider 104 to the pharmacy via the web portal interface 109, or via other electronic or non-electronic communications. In addition, the service provider 104 may also deliver, or otherwise direct delivery of, a recall message 207 that includes the recall information to a recall logistics entity 202. The recall message 207 may also identify the pharmacy location that holds the affected or recalled drug or product inventory.

In an example embodiment of the invention, the recall logistics entity 202 may be an entity that handles reverse logistics associated with a recall, including obtaining, recovering, and/or destroying the recalled drug or product. The recall logistics entity 202 may be an entity that is distinct from the pharmacy, service provider, or claims processor described herein. However, the reverse logistics entity 202 may also be owned, operated, or otherwise associated with one or more of the pharmacy, service provider, or claims processor without departing from example embodiments of the invention.

In block 316, in response to receiving the recall message 207, the recall logistics entity 202 may remove the affected or recalled drug or product inventory from the pharmacy location. For example, the recall logistics entity 202 may physically send a representative to the pharmacy location to remove the affected or recalled drug or product inventory. In another embodiment, the recall logistics entity 202 may verify that an individual at the pharmacy location has disposed of the affected or recalled drug or product inventory such that the inventory cannot be resold. In yet another example embodiment, the recall logistics entity 202 may also deliver a shipping label to the pharmacy via electronic communication means (e.g., facsimile, email, Internet webpage, etc.) or non-electronic delivery means (e.g., postal mail). The shipping label may be prepaid and include an address of a return location specified by the recall logistics entity 202, according to an example embodiment of the invention. It will also be appreciated that the shipping label may likewise be provided by the service provider 104 to the pharmacy on behalf of the recall logistics entity 202. For example, the shipping label may be available to the pharmacy via the web portal interface 109. The pharmacy may then print out the shipping label for use in returning the affected or recalled inventory to the recall logistics entity 202 or another entity.

In order to obtain reimbursement for the affected or recalled inventory, the pharmacy computer 103 may submit a claim request 208 to the service provider 104, as provided in block 318. The claim request 208 may include drug information (e.g., NDC, quantity) corresponding to the affected or recalled inventory of the drug or product. In addition, the claim request 208 may include a BIN/PCN designated for a drug or product recall. In block 320, the service provider 104 may deliver the claim request 208 to an appropriate claims processor corresponding to the BIN/PCN included in the claim request 208. In an example embodiment, the BIN/PCN associated with the drug or product recall may designate an internal claims processor that is actually part of the service provider 104, and the delivery of the claim request 208 may be an internal delivery. Alternatively, the BIN/PCN may designate an external claims processor, and the delivery of the claim request 208 may be an external delivery or routing, perhaps via network 110.

In block 320, the claims processor may adjudicate the claim request 208 and generate a claim response 212. The service provider 104 may deliver the claim response 212 to the pharmacy computer 103. As indicated in the claim response 212, the pharmacy may be reimbursed for the affected or recalled inventory. In an example embodiment, the reimbursement amount may be funded by the pharmaceutical manufacturer or another entity. It will be appreciated that the reimbursement amount may be at or near the pharmacy's acquisition cost, the pharmacy's Usual and Customary (U&C) cost, or yet another amount. Many variations of the reimbursement amount are available in accordance with example embodiments of the invention. It will also be appreciated that the reimbursement amount specified in the claim response 212 may be provisional until the recall logistics entity 202 verifies to the service provider 104 that the affected or recalled inventory has actually been recovered or received from the pharmacy.

Figure 2B:
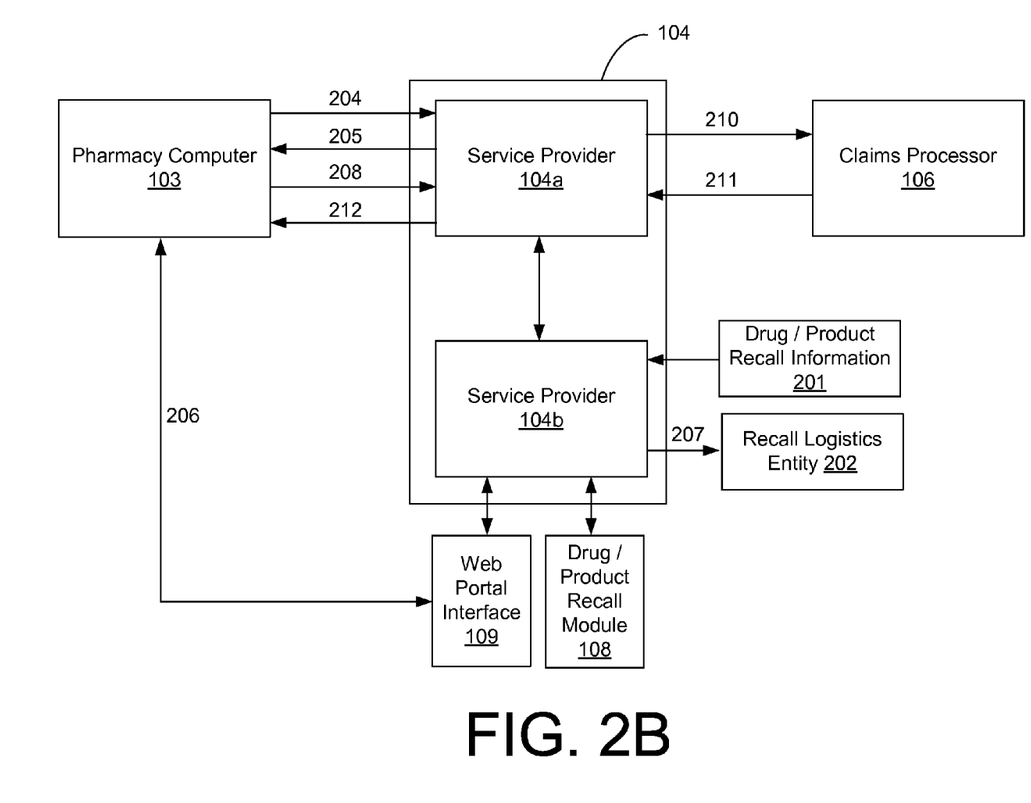
FIG. 2B illustrates a block diagram for another example drug or product recall process, according to an example embodiment of the invention.

FIG. 2B illustrates a variation of the block diagram of FIG. 2A that has been discussed in conjunction with FIGS. 3A-3B. As shown by FIG. 2B, the service provider 104 may be comprised of two or more distinct service providers 104a and 104b that are in communication with each other. Service provider 104a may be operative with the pharmacy computer 103 and claims processor 106 while service provider 104b may be operative with other pharmacy computers and claims processors. However, service provider 104b may have a data processing arrangement with service provider 104a. Under the data processing agreement, the service provider 104a may be permitted to utilize or offer services of the service provider 104b, including the business rules described above or the web portal interface 109. Accordingly, the services of the service provider 104b, including the drug/product recall module 108 and web portal interface 109, may be available to the pharmacy computer 103 via the service providers 104a and 104b.

The invention is described above with reference to block and flow diagrams of systems, methods, apparatuses, and/or computer program products according to example embodiments of the invention. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments of the invention.

These computer-executable program instructions may be loaded onto a general purpose computer, a special-purpose computer, a processor, or other programmable data processing apparatus to produce a particular machine, such that the instructions that execute on the computer, processor, or other programmable data processing apparatus create means for implementing one or more functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks. As an example, embodiments of the invention may provide for a computer program product, comprising a computer usable medium having a computer readable program code or program instructions embodied therein, said computer readable program code adapted to be executed to implement one or more functions specified in the flow diagram block or blocks. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks.

Accordingly, blocks of the block diagrams and flow diagrams support combinations of means for performing the specified functions, combinations of elements or steps for performing the specified functions and program instruction means for performing the specified functions. It will also be understood that each block of the block diagrams and flow diagrams, and combinations of blocks in the block diagrams and flow diagrams, can be implemented by special-purpose, hardware-based computer systems that perform the specified functions, elements or steps, or combinations of special purpose hardware and computer instructions.

Many modifications and other embodiments of the invention set forth herein will be apparent having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A method, comprising:
receiving, by at least one service provider computer, a healthcare transaction request from a pharmacy computer associated with a pharmacy, wherein the healthcare transaction request includes an identification of a prescribed drug or product for a patient;
determining, by the at least one service provider computer based upon the identification of the prescribed drug or product, that the prescribed drug or product is associated with a recall;
providing, by the at least one service provider computer to the pharmacy computer in response to the determination that the prescribed drug or product is associated with the recall, a response that includes information for accessing a web portal interface;
subsequent to providing the response, receiving, by the at least one service provider computer from a pharmacy computer over the web portal interface, lot numbers associated with pharmacy inventory of the prescribed drug or product;
determining, by the at least one service provider computer, that one or more of the received lot numbers are affected by the recall;
generating, by the at least one service provider computer, a notification identifying the determined lot numbers that are affected by the recall;
directing, by the at least one service provider computer, a delivery of the notification to a recall logistics entity, wherein the delivered notification enables the recall logistics entity to obtain the recalled pharmacy inventory corresponding to the received lot numbers identified in the notification; and
directing, by the at least one service provider computer, a claim request for a reimbursement amount for the recalled pharmacy inventory, wherein the pharmacy is reimbursed the reimbursement amount following verification that the recalled pharmacy inventory has been obtained by the recall logistics entity from the pharmacy.

2. The method of claim 1, wherein the healthcare transaction request is associated with a pharmacy claim transaction.

3. The method of claim 1, wherein a shipping label is provided to the pharmacy, and wherein the shipping label enables the pharmacy to deliver the recalled pharmacy inventory to the recall logistics entity.

4. The method of claim 1, wherein the response further includes an access code or transaction ID identifying the pharmacy, a transaction, or the prescribed drug or product, and further comprising:
receiving, by the at least one service provider computer via the web portal interface, the access code or transaction ID;
validating, by the at least one service provider computer, the access code or transaction ID; and
requesting, by the at least one service provider computer via the web portal interface, lot numbers associated with the pharmacy inventory of the prescribed drug or product.

5. The method of claim 1, wherein the healthcare transaction request is received by the at least one service provider computer from the pharmacy computer over a first network, and wherein the web portal interface is accessible by the pharmacy computer over a second network different from the first network.

6. The method of claim 5, wherein the first network is a healthcare transaction processing network, and wherein the second network is an Internet.

7. The method of claim 1, wherein the information for accessing a web portal interface includes a website address associated with the web portal interface.

8. The method of claim 1, wherein the response is of a predetermined alert type, and wherein subsequent to the at least one service provider computer receiving the lot numbers via the web portal interface, the at least one service provider computer adjusts messaging preferences associated with the pharmacy, wherein in accordance with the adjusted messaging preferences, the at least one service provider computer does not provide future responses of the predetermined alert type to the pharmacy computer for at least a period of time.

9. The method of claim 1, wherein directing the claim request includes delivering the claim request to a claims processor for adjudication.

10. The method of claim 1, wherein the claim request is received by the at least one service provider computer from the pharmacy computer prior to directing the claim request for the reimbursement amount.

11. A system, comprising:
a memory for storing computer-executable instructions; and
a processor configured to access the memory and further configured to execute the computer-executable instructions to:
receive a healthcare transaction request from a pharmacy computer associated with a pharmacy, wherein the healthcare transaction request includes an identification of a prescribed drug or product for a patient;
determine, based upon the identification of the prescribed drug or product, that the prescribed drug or product is associated with a recall;
provide, to the pharmacy computer in response to the determination that the prescribed drug or product is associated with the recall, a response that includes information for accessing a web portal interface;
subsequent to providing the response, receive, over the web portal interface, lot numbers associated with pharmacy inventory of the prescribed drug or product;
determine that one or more of the received lot numbers are affected by the recall;
generate a notification identifying the determined lot numbers that are affected by the recall;
direct a delivery of the notification to a recall logistics entity, wherein the delivered notification enables the recall logistics entity to obtain the recalled pharmacy inventory corresponding to the received lot numbers identified in the notification; and
direct a claim request for a reimbursement amount for the recalled pharmacy inventory, wherein the pharmacy is reimbursed the reimbursement amount following verification that the recalled pharmacy inventory has been obtained by the recall logistics entity from the pharmacy.

12. The system of claim 11, wherein the healthcare transaction request is associated with a pharmacy claim transaction.

13. The system of claim 11, wherein a shipping label is provided to the pharmacy, and wherein the shipping label enables the pharmacy to deliver the recalled pharmacy inventory to the recall logistics entity.

14. The system of claim 11, wherein the response further includes an access code or transaction ID identifying the pharmacy, a transaction, or the prescribed drug or product, and wherein the processor is further configured to execute the computer-executable instructions to:
receive, via the web portal interface, the access code or transaction ID;
validate the access code or transaction ID; and
request, via the web portal interface, lot numbers associated with the pharmacy inventory of the prescribed drug or product.

15. The system of claim 11, wherein the healthcare transaction request is received by the processor from the pharmacy computer over a first network, and wherein the web portal interface is accessible by the pharmacy computer over a second network different from the first network.

16. The system of claim 15, wherein the first network is a healthcare transaction processing network, and wherein the second network is an Internet.

17. The system of claim 11, wherein the information for accessing a web portal interface includes a website address associated with the web portal interface.

18. The system of claim 11, wherein the response is of a predetermined alert type, and wherein subsequent to the processor receiving the lot numbers via the web portal interface, the processor is configured to adjust messaging preferences associated with the pharmacy, wherein in accordance with the adjusted messaging preferences, the processor is configured to not provide future responses of the predetermined alert type to the pharmacy computer for at least a period of time.

19. The system of claim 11, wherein the claim request is directed by delivering the claim request to a claims processor for adjudication.

20. The system of claim 11, wherein the processor is configured to execute the computer-executable instructions to receive the claim request from the pharmacy computer prior to directing the claim request for the reimbursement amount.

* * * * *